US008622939B2

(12) United States Patent
Nguyen

(10) Patent No.: US 8,622,939 B2
(45) Date of Patent: Jan. 7, 2014

(54) APPARATUS FOR MANIPULATING JOINTS OF A LIMB

(75) Inventor: Chau Hoang Thanh Nguyen, Heidelberg Heights (AU)

(73) Assignee: BES Rehab Ltd., Bristol (GB)

( * ) Notice: Subject to any disclaimer, the term of this patent is extended or adjusted under 35 U.S.C. 154(b) by 468 days.

(21) Appl. No.: 12/876,041

(22) Filed: Sep. 3, 2010

(65) Prior Publication Data

US 2012/0059291 A1 Mar. 8, 2012

(51) Int. Cl.

| | |
|---|---|
| ***A61H 1/02*** | (2006.01) |
| ***A61H 1/00*** | (2006.01) |
| ***A63B 23/16*** | (2006.01) |
| ***A61F 5/00*** | (2006.01) |

(52) U.S. Cl.
USPC ......... 601/40; 601/5; 482/44; 482/47; 602/22

(58) Field of Classification Search
USPC ............. 601/5, 15, 18, 23, 26, 27, 29, 33, 40, 601/41, 44, 84, 87, 97, 98, 101, 103, 112, 601/113; 623/24, 26; 482/1–9, 44, 47, 48, 482/79, 80; 2/16, 20, 21, 159, 160, 161.1, 2/161.6, 163; 602/20–22; 401/7, 8
See application file for complete search history.

(56) References Cited

U.S. PATENT DOCUMENTS

| | | | | |
|---|---|---|---|---|
| 3,564,673 | A * | 2/1971 | Daddona | 24/578.17 |
| 3,694,021 | A * | 9/1972 | Mullen | 294/106 |
| 4,765,320 | A * | 8/1988 | Lindemann et al. | 602/22 |
| 4,875,469 | A * | 10/1989 | Brook et al. | 601/40 |
| 5,178,137 | A * | 1/1993 | Goor et al. | 601/40 |
| 5,516,249 | A * | 5/1996 | Brimhall | 414/5 |
| 5,683,351 | A * | 11/1997 | Kaiser et al. | 601/40 |
| 5,865,770 | A * | 2/1999 | Schectman | 601/23 |
| 6,647,597 | B2 * | 11/2003 | Reiter | 24/303 |
| 7,370,368 | B2 * | 5/2008 | Motooka et al. | 2/19 |
| 7,823,760 | B2 * | 11/2010 | Zemlok et al. | 227/175.1 |
| 8,255,079 | B2 * | 8/2012 | Linn et al. | 700/213 |
| 8,348,810 | B2 * | 1/2013 | Land et al. | 482/47 |
| 2003/0073939 | A1 * | 4/2003 | Taylor et al. | 601/40 |
| 2003/0162634 | A1 * | 8/2003 | Farrell et al. | 482/47 |
| 2003/0195093 | A1 * | 10/2003 | White | 482/124 |
| 2003/0218105 | A1 * | 11/2003 | Sones et al. | 248/104 |
| 2004/0258471 | A1 * | 12/2004 | Granata | 403/381 |
| 2006/0205526 | A1 * | 9/2006 | Whitehead et al. | 473/59 |
| 2006/0211964 | A1 * | 9/2006 | Farrell et al. | 602/5 |
| 2007/0083968 | A1 * | 4/2007 | Stokes | 2/16 |
| 2007/0191743 | A1 * | 8/2007 | McBean et al. | 601/5 |
| 2008/0282445 | A1 * | 11/2008 | Taliento et al. | 2/161.3 |
| 2010/0248676 | A1 * | 9/2010 | Takahashi | 455/341 |
| 2012/0059290 | A1 * | 3/2012 | Yip | 601/40 |

* cited by examiner

*Primary Examiner* — Justine Yu
*Assistant Examiner* — Christopher Miller
(74) *Attorney, Agent, or Firm* — Timberline Patent Law Group PLLC

(57) ABSTRACT

An apparatus for applying movement to the joints of a human patient is provided. The apparatus includes an exoskeleton assembly with segments that can be secured to the patient. One or more motor modules are removably coupled to a supporting structure of the exoskeleton assembly, and each motor module includes multiple motor drives. A plurality of actuating members is operatively connected to each motor module. A first end of each actuating member is connected to one of the motor drives and a second end of each actuating member is coupled to a segment of the exoskeleton assembly. Each actuating member can be driven by a respective motor drive to impart movement in multiple degrees of freedom to individual joints.

15 Claims, 7 Drawing Sheets

APPARATUS FOR MANIPULATING JOINTS OF A LIMB

FIELD OF THE INVENTION

The invention, in general, relates to power assisted therapeutic devices. More specifically, the invention relates to an apparatus for manipulating joints of a limb of a patient.

BACKGROUND OF THE INVENTION

Healthy working joints are of utmost importance in providing functional use of limbs and ultimately independence in an individual's life. The loss of joint functions result is a severe compromise of the ability to feed and care for oneself, and limits one's participation in work, social, and family life. Several injuries, diseases, and neurological disorders causing deformations of a limb or digits of the limb may result in loss of joint functions. These include paralysis (from central or peripheral nerve injuries), swelling, joint stiffness, pain, burns, scarring or broken bones. Such deformations often inhibit muscular, structural, or neurological functions of the limb or the digits of the limb, resulting in an individual's inability in carrying out day-to-day activities. Such individuals, who are recovering from problems affecting the limb, need vigilant, appropriate and effective therapy of the limbs, to improve the outcome of the healing process significantly and the restoration of joint functions. Therefore, in order to recuperate the probability of mobility in a deformed limb including loss of joint range of motion, physicians often advise practicing Continuous Passive Motion (CPM) techniques.

CPM is a form of therapy commonly prescribed for assisting the optimal healing of joints and connective tissue following damage and pathology. CPM therapy is often prescribed and used for rehabilitating larger joints such as, the knee, ankle, shoulder, elbow and hip to achieve positive results. It is easier to administer CPM therapy to singular, large joints that can be isolated. However, for rehabilitating small multiple joints of the hand, although CPM therapy has been proven beneficial, the therapy is seldom prescribed or used. Typically, CPM devices allow manipulation of the digits.

However, effective control over phalanx sections of the digits, ensuring safe and consistent delivery of controlled manipulation and forces to multiple joints at the same time, is essential in order to achieve good results with CPM. Further, an individual requiring rehabilitation of limbs requires ease of attachment of CPM devices to fingers, address each joints individually, and the ability of sensing digit flexibility. Hence, the therapeutic device for manipulating the digits of the limb needs a safety feature for preventing over delivery of forces to the digits of the limb, thereby averting rupture of a digit.

Accordingly, there is a need for an apparatus to manipulate joints of a limb of a patient in a more controlled, safe and effective manner. There is also a need for the apparatus to enable independent manipulation of each limb segment.

BRIEF DESCRIPTION OF THE FIGURES

The accompanying figures where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
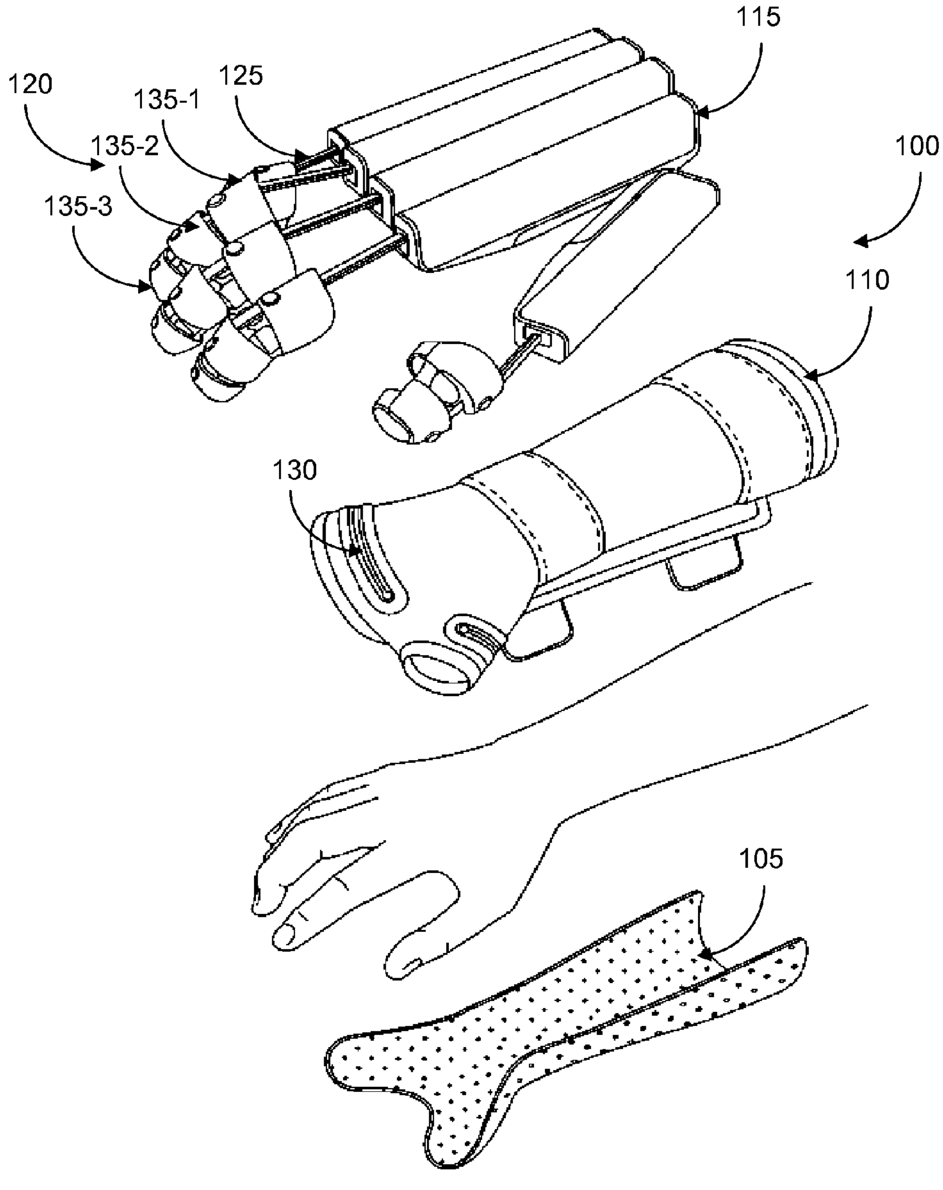
FIG. 1 illustrates a disassembled view of an apparatus for manipulating joints of a limb of a patient in accordance with an embodiment of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

Definition Of Terms

This section includes following definitions of selected terms employed herein. The definitions include various examples and/or forms of components that fall within the scope of a term and that may be used for implementation. The examples provided herein are not intended to be limiting. Both singular and plural forms of these terms may be within the definitions.

Limb segment: In a human body, a limb segment, such as, an arm or a leg is an appendage used for locomotion or grasping.

Joint of a limb: A location, at which two or more bones in a limb segment make contact, is a joint of a limb.

Digit: In a human body, a digit is a finger or a toe.

Phalanx segment: each bone in a digit is a phalanx segment.

Proximal phalanx: a proximal phalanx is a bone in a digit located at the base of a digit.

Distal phalanx: a distal phalanx is a bone in a digit located at the tip of a digit.

Intermediate phalanx: an intermediate phalanx is a bone in a digit located between a proximal phalanx and a distal phalanx.

Metacarpophalangeal (MCP) joint: is a joint in a digit that connects a metacarpal bone in a palm to a proximal phalanx.

Proximal Interphalangeal (PIP) joint: is a joint in a digit that connects a proximal phalanx to an intermediate phalanx.

Distal Interphalangeal (DIP) joint: is a joint in a digit that connects an intermediate phalanx to a distal phalanx.

DETAILED DESCRIPTION OF THE INVENTION

Before describing in detail embodiments that are in accordance with the invention, it should be observed that the embodiments reside primarily in combinations of apparatus components related to manipulating one or more joints of a limb of a patient. Accordingly, the apparatus components have been represented where appropriate by conventional symbols in the drawings, showing only those specific details that are pertinent to understanding the embodiments of the invention so as not to obscure the disclosure with details that will be readily apparent to those of ordinary skill in the art having the benefit of the description herein. Thus, it will be appreciated that for simplicity and clarity of illustration, common and well-understood elements that are useful or necessary in a commercially feasible embodiment may not be depicted in order to facilitate a less obstructed view of these various embodiments.

In this document, relational terms such as first and second, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Pursuant to various embodiments disclosed herein, the invention provides an apparatus for manipulating joints of a limb of a patient. The limb of the patient comprises a plurality of limb segments. Each limb segment of the plurality of limb segments connects one or more joints. The apparatus includes one or more motor modules removably coupled to a supporting structure configured on the limb. Each motor module includes a plurality of motor drives. The apparatus also includes a manipulating exoskeleton assembly comprising a plurality of exoskeleton segments. An exoskeleton segment of the plurality of exoskeleton segments is removably secured on the limb segment. Further, a plurality of actuating members is operatively connected to each motor module of the one or more motor modules. A first end of each actuating member is operatively connected to a motor drive of a motor module and a second end is removably coupled to an exoskeleton segment of the plurality of exoskeleton segments. Each actuating member is driven by a motor drive operatively connected to each actuating member thereby transmitting push and pull forces to a limb segment associated with each actuating member. Thus, each of the plurality of limb segments is moved to independently manipulate the joints of the limb.

FIG. 1 illustrates a disassembled view of an apparatus 100 for manipulating joints of a limb of a patient in accordance with an embodiment of the invention. The limb may be for example, but not limited to a hand, a knee, a finger, an ankle, a shoulder, an elbow, a thigh, a forearm and so on. FIG. 1 illustrates a hand of a patient and apparatus 100 is shown as used for manipulating finger joints of the hand for purpose of ease in explanation. However, it will be apparent to a person skilled in the art that apparatus 100 may be utilized for manipulating any other limbs of the patient.

The limb of the patient comprises a plurality of limb segments. Each limb segment of the plurality of limb segments connects the one or more joints. For example, a limb segment i.e., a proximal phalanx of a finger or a digit connects a metacarpophalangeal joint and a proximal interphalangeal joint of the digit.

Apparatus 100 is a therapeutic device used for performing tasks including, but not limited to, independently manipulating each joint of the limb of the patient according to established physiotherapeutic regimes, monitoring the patient's ability to move the limb, and providing functional power assistance to manipulate each joint of the limb to perform day-to-day activities.

Apparatus 100 includes a supporting structure configured on the limb of the patient. The supporting structure includes a splint support 105 and a splint pad 110. In an embodiment, splint support 105 may be composed of a thermoplastic material. Further, splint pad 110 may be composed of a rubber material. The rubber material used for splint pad 110 may be for example, neoprene. However, it will be apparent to a person skilled in the art that splint support 105 and splint pad 110 may be composed of any other materials known in the art. Splint support 105 may be customized according to the shape of the limb. For example, splint support 105 may be formed using thermoplastic sheets. These thermoplastic sheets may be molded according to the shape of a hand, a wrist, and a forearm of a patient.

Splint pad 110 may be formed in predetermined universal sizes, for example, small, medium, and large. In an embodiment, splint pad 110 may include fastening members for securely configuring the support structure on the limb. Thus, splint pad 110 and splint support 105 may be securely configured on the limb using the fastening members.

Apparatus 100 also includes one or more motor modules such as, a motor module 115, a plurality of manipulating exoskeleton assemblies such as, a manipulating exoskeleton assembly 120, and a plurality of actuating members such as, an actuating member 125. The one or more motor modules are mounted onto splint pad 110. In an embodiment, in order to mount the one or motor modules onto splint pad 110, a guide way 130 is provided. Guide way 130 is provided on an upper surface of splint pad 110 as shown in FIG. 1. A guide way such as, guide way 130 may be a continuous guide way as shown in FIG. 1. However, it will be apparent to a person skilled in the art that the guide way may have different configurations such as, a guide hole. In this case, each motor module of the one or more motor modules may include a coupling member capable of coupling each motor module with guide way 130 to secure the one or more motor modules on splint pad 110. For example, motor module 115 may be mounted on splint pad 110 by inserting a coupling member of motor module 115 into guide way 130 and moving the coupling member through guide way 130. By moving the coupling member through guide way 130, motor module 115 may be placed in an appropriate position on splint pad 110. Each motor module is independent of another and mounted accordingly on splint pad 110, thereby facilitating manipulation of each joints independently.

In an embodiment, a coupling member of a motor module of the one or more motor modules may be a stud arrangement (not shown in FIG. 1). In this case, the stud arrangement of the motor module may interlock with guide way 130 to securely mount the motor module on splint pad 110. Alternatively, the coupling member used for mounting the motor module on splint pad 110 may be a magnetic ball segment mount (not shown in FIG. 1). The magnetic ball segment mount provides an angular freedom for the motor module secured on splint pad 110. The magnetic ball segment mount is explained in detail in conjunction with FIG. 7A and FIG. 7B.

Each motor module of the one or more motor module includes a plurality of motor drives. Motor module 115 comprises a plurality of motor drives. Each motor drive independently manipulates a joint of the limb using the plurality of actuating members operatively connected to each motor module. The plurality of motor drives are set up in a stacked arrangement. In the stacked arrangement, a child motor drive is displaced by a parent motor drive thereby enabling a limb segment associated with the child motor drive to move with respect to a limb segment associated with the parent motor drive. In an embodiment, setting up the plurality of motor drives in a stacked arrangement involves arranging the plurality of motor drives in a nested fashion. The arrangement of the one or more motor drives in a nested fashion is explained in detail in conjunction with FIG. 3. In another embodiment, setting up the plurality of motor drives in a stacked arrangement involves arranging the plurality of motor drives in a pyramid fashion. The arrangement of the one or more motor drives in a pyramid fashion is explained in detail in conjunction with FIG. 4.

Each motor module of the one or more motor modules are connected to a manipulating exoskeleton assembly of the plurality of manipulating exoskeleton assemblies using the plurality of actuating members for manipulating a joint of the limb. Each manipulating exoskeleton assembly comprises a plurality of exoskeleton segments. Each exoskeleton segment of the plurality of exoskeleton segments is removably secured on a limb segment. For example, manipulating exoskeleton assembly 120 comprises an exoskeleton segment 135-1, an exoskeleton segment 135-2 and an exoskeleton segment 135-3.

Further, an actuating member of the plurality of actuating members includes a first end and a second end. The first end of the actuating member may be connected to a motor drive of a motor module of the one or more motor modules. Whereas the second end of the actuating member may be connected to an exoskeleton segment of the plurality of exoskeleton segments.

Manipulating exoskeleton assembly 120 is connected to motor module 115 using the plurality of actuating members such as, actuating member 125. Thus, plurality of actuating members may be operatively connected to exoskeleton segment 135-1, exoskeleton segment 135-2 and motor module 115. More specifically, a first end of actuating member 125 may be operatively connected to a motor drive of motor module 115. A second end of actuating member 125 is removably coupled to an exoskeleton segment of the plurality of exoskeleton segments. The connection between a motor module, an actuating member and an exoskeleton segment is explained in detail in conjunction with FIG. 2.

The actuating member of the plurality of actuating members may be a flexible thin gauge strip that transmits the push and pull forces required to manipulate each joints of the limb. In an embodiment, the actuating member may be composed of a highly pliable material with low or zero linear compressibility and linear expansion. For example, an actuating member may be composed of a metal alloy such as, Nitinol. Nitinol is composed of Nickel and Titanium. However, it will be apparent to a person skilled in the art that the actuating member may be composed of any other materials known in the art.

During operation, each actuating member of the plurality of actuating members is driven by a motor module of the one or more motor modules, Thereafter, each actuating member transfers push and pull forces on a limb segment associated with each actuating member to the move the limb segment. For example, actuating member 125 may be operatively connected to exoskeleton segment 135-1. Exoskeleton segment 135-1 may be removably secured on a distal phalanx segment of a digit of the hand. Then, actuating member 125 may apply push and pull forces on exoskeleton segment 135-1 upon being driven by motor module 115. Consequently, the distal phalanx segment moves with respect to a distal interphalangeal joint of the digit based on the push and pull forces. Thus, the movement of actuating member 125 manipulates the distal interphalangeal joint. The motor module and the method of manipulating the joints of the limb using the motor module are further explained in detail in conjunction with FIG. 2.

Apparatus 100 may further include a central control unit (CCU) (not shown in FIG. 1) for controlling the manipulation of the joints of the limb. The CCU may be mounted on splint pad 110 of the supporting structure. The CCU may be electronically coupled to each motor module of the one or more motor modules in order to control the one or more motor modules. The CCU is configured to assess and control the manipulation of a limb segment by measuring forces generated at a motor module while manipulating the limb segment and measuring displacement of the motor module while manipulating the limb segment. The CCU forces generated at the motor module may be measured using a plurality of force sensors. Further, the displacement of the motor drive during manipulation may be measured using a plurality of displacement sensors. The measurement of forces generated at a motor drive and displacement of the motor drive during manipulation using force sensors and displacement sensors, is further explained in detail in conjunction with FIG. 2.

In an embodiment, the CCU provides a physiotherapeutic regime for manipulating the joints of the limb. The physiotherapeutic regime may be translated into a set of instructions. The CCU provides the set of instructions to each motor module such as motor module 115 for synchronously controlling movement of each joint of the limb. The movement of each joint of the limb enables flexing and extending the plurality of limb segments. The CCU is further configured to determine at least one of an absolute position, an absolute angular position, and range of manipulation associated with the limb segment during the manipulation of the limb segment. Additionally, the CCU also distributes power, sends control signals, logs data, and allows for manual intervention in manipulating the joints. Therefore, the CCU provides functional power assistance to manipulate each joint of the limb to perform day-to-day activities. In an embodiment, the CCU may incorporate a battery and a communication interface. Furthermore, apparatus 100 interacts with a computer system in order to upload and download data. For example, the CCU is connected to a personal computer for uploading a physiotherapeutic regime and downloading data associated with the patient. Thereafter, the CCU controls the one or more motor modules for manipulating the joints of the limb.

Figure 2:
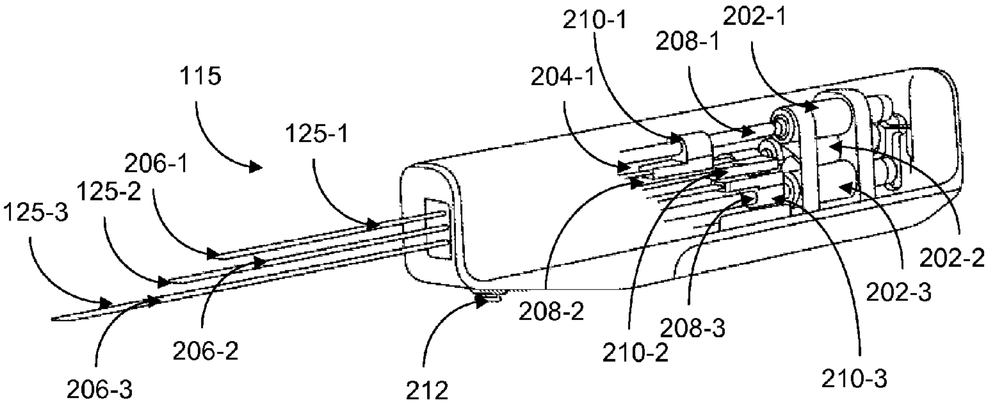
FIG. 2 illustrates an inner view of a motor module including a plurality of motor drives enclosed therewithin in accordance with an embodiment of the invention.

FIG. 2 illustrates an inner view of motor module 115 including the plurality of motor drives enclosed therewithin in accordance with an embodiment of the invention. Motor module 115 secured on the supporting structure delivers forces for manipulating joints of the limb of the patient. Motor module 115 includes a plurality of motor drives 202 that generates and delivers forces to each joints of the limb. As shown in FIG. 2, plurality of motor drives 202 may include a motor drive 202-1, a motor drive 202-2 and a motor drive 202-3. It will be apparent to a person skilled in the art that motor module 115 is shown to include three motor drives for purpose of description. However, motor module 115 may include more than three motor drives. Plurality of motor drives 202 may be arranged in different fashions for delivering the push and pull forces to each joints of the limb. This is explained in conjunction with FIG. 3 and FIG. 4.

Each motor drive of the one or more motor drives may be operatively connected to an actuating member. The actuating member may have a first end and a second end. The actuating member may have the first end operatively connected to a motor drive of the one or more motor drives and the second end connected to an exoskeleton segment of a manipulating exoskeleton assembly. For example by considering the limb as a digit, actuating member 125-1 may have a first end 204-1 operatively connected to motor drive 202-1 and a second end 206-1 connected to an exoskeleton segment disposed on a proximal phalanx of the digit. Similarly, actuating member 125-2 may have a first end 204-2 (not shown) operatively connected to motor drive 202-2 and a second end 206-2 connected to an exoskeleton segment disposed on an intermediate phalanx of the digit. Further, actuating member 125-3 may have a first end 204-3 (not shown) operatively connected to motor drive 202-3 and a second end 206-3 connected to an exoskeleton segment disposed on a distal phalanx of the digit.

A motor drive of the plurality of motor drives may be operatively connected to an actuating member using a linear actuator for example. Thus, apparatus 100 may include a plurality of linear actuators. A linear actuator of the plurality of linear actuators is operatively connected to the motor drive of the plurality of motor drives. The linear actuator is also connected to the actuating member of the plurality of actuating members. The motor drive is capable of driving the linear actuator in a linear direction thereby enabling the actuating member to move in the linear direction.

In an embodiment, each motor drive of the one or more motor drives may have a linear actuator such as, a lead screw arrangement. The lead screw arrangement includes a lead screw based linear actuator and a nut operatively engaged with the lead screw based linear actuator. In an alternate embodiment, a rack and pinion type linear actuator may be used for operatively connecting a motor drive of the plurality of motor drives to an actuating member. The lead screw based linear actuator, hereinafter referred to as a "lead screw", is operatively connected to the motor drive at one end. Further, the actuating member is removably coupled to the nut. More specifically, a first end of the actuating member may be removably connected to the nut. When the motor drive operates, the lead screw rotates and converts the rotary motion into a linear motion. Thus, the nut linearly moves along the length of the lead screw. Consequently, the actuating member moves forward in a linear direction in response to the linear motion of the nut. It will be apparent to a person skilled in the art that apparatus 100 may include any other linear actuators known in the art operatively connected to the plurality of motor drives for moving the actuating members of apparatus 100.

For example, a lead screw 208-1 operatively connected to motor drive 202-1 may be driven by motor drive 202-1. Lead screw 208-1 may rotate to move a nut 210-1 operatively connected to lead screw 208-1 in a linear direction. In response to the linear motion of nut 210-1, actuating member 125-1 connected to nut 210-1 moves in a linear direction. Similarly, lead screw 208-2 may rotate to move a nut 210-2 operatively connected to lead screw 208-2 in a linear direction. In response to the linear motion of nut 210-2, actuating member 125-2 connected to nut 210-2 moves in a linear direction. Further, lead screw 208-3 may also rotate to move a nut 210-3 operatively connected to lead screw 208-3 in a linear direction. In response to the linear motion of nut 210-3, actuating member 125-3 connected to nut 210-3 moves in a linear direction. During the movement of nut 210-1, nut 210-2 and nut 210-3 in the linear direction, each of these nuts may not interfere with each other. For example, nut 210-1 may not interfere with nut 210-2 and similarly nut 210-2 may not interfere with nut 210-3.

Once each of the actuating members, such as actuating member 125-1, actuating member 125-2 and actuating member 125-3 move in a linear direction, push and pull forces are applied on a manipulating exoskeleton assembly disposed on the respective phalanges of the digit. Thus, the digit curves or folds itself when the push and pull forces are applied on the digit. More specifically, joints of the digit, flex when the push forces are applied and extend when the pull forces are applied.

Further, each of the phalanges of the digit may be independently manipulated. For example, a motor drive 202-3 drives lead screw 208-3 operatively connected to motor drive 202-3. In response, lead screw 208-3 rotates to move a nut 210-3 operatively connected to lead screw 208-3 in a linear direction. Thereafter, actuating member 125-3 connected to nut 210-3 moves in a linear direction to move the distal phalanx. Moving the distal phalanx by activating motor drive 202-3, in turn enables independent flexion and extension of the distal interphalangeal (DIP) joint. While motor drive 202-3 operates, motor drive 202-1 and motor drive 202-2 may remain idle or non-operative. Thus, the proximal phalanx or the intermediate phalanx does not move thereby achieving independent movement of the distal phalanx.

Additionally, each joint of a digit, i.e. metacarpophalangeal (MCP) joint and proximal interphalangeal (PIP) joint may also be manipulated independently. For example, motor drive 202-2 and motor drive 202-3 operate together to move lead screw 208-2 and lead screw 208-3 in a linear direction. The linear movement of lead screw 208-2 and lead screw 208-3 causes the intermediate phalanx to flex, while the distal phalanx maintains a relative angle with respect to the intermediate phalanx. The movement of the intermediate phalanx, in turn enables independent flexion and extension of the PIP joint. Similarly, motor drive 202-1, motor drive 202-2, and motor drive 202-3 operate together to move lead screw 208-1, lead screw 208-2, and lead screw 208-3 in a linear direction. The linear movement of lead screw 208-1, lead screw 208-2, and lead screw 208-3 causes the proximal phalanx to flex, while the intermediate phalanx and the distal phalanx maintain a relative angle with respect to the proximal phalanx. Once the proximal phalanx moves, independent flexion and extension of the MCP joint is achieved.

While manipulating each limb segment of the limb, each motor drive of the plurality of motor drives experiences or generates forces. For example, while manipulating each phalanx segments of a digit, each motor drive associated with a phalanx segment experiences or generates forces. Therefore, each motor drive may have force sensors and displacement sensors to measure forces generated at each motor drive and displacement of each motor drive during manipulation. For example, in motor module 115, a plurality of force sensors (not shown in FIG. 2) may be coupled to a motor housing of a motor drive. A force sensor of the plurality of force sensors measures forces generated at the motor drive during manipulation of a limb segment associated with the motor drive. The force may be measured by determining a torque applied at the limb. For example, a strain gauge sensor may be operatively coupled to the motor housing of the motor drive using a set of sensor wires i.e., a flexible-printed-circuit. The strain gauge sensor measures forces generated at the motor drive during manipulation of the limb segment associated with the motor drive by determining a strain experienced on the motor housing by the forces generated or experienced at the motor drive. The forces measured at the strain gauge sensor are communicated to the CCU. The CCU then measures the forces generated at the motor drive to assess the manipulation of the limb segment.

Further, the plurality of displacement sensors may also be operatively coupled to the motor housing. A displacement sensor of the plurality of displacement sensors measures a linear displacement of the motor drive during manipulation of a limb segment associated with the motor drive. The linear displacement is measured to determine an angular position of the one or more joints of the limb. The linear displacement measurements determined may be communicated to the CCU. Then the CCU may determine an absolute displacement of the motor drive, an absolute force of the motor drive, an absolute angle between the joints of the limb, and an absolute torque applied at the limb using the linear displacement measurements.

Referring back to motor module 115, motor module 115 of the one or more motor modules is removably coupled to the supporting structure using a stud arrangement 212 as shown in FIG. 2. In an embodiment, a magnetic ball segment mount is used for removably coupling motor module 115 to the supporting structure. Alternatively, a buckle arrangement may also be used for removably coupling motor module 115 to the supporting structure. Stud arrangement 212 for removably coupling motor module 115 to the supporting structure is explained in further detail in conjunction with FIG. 7A and FIG. 7B.

Figure 3:
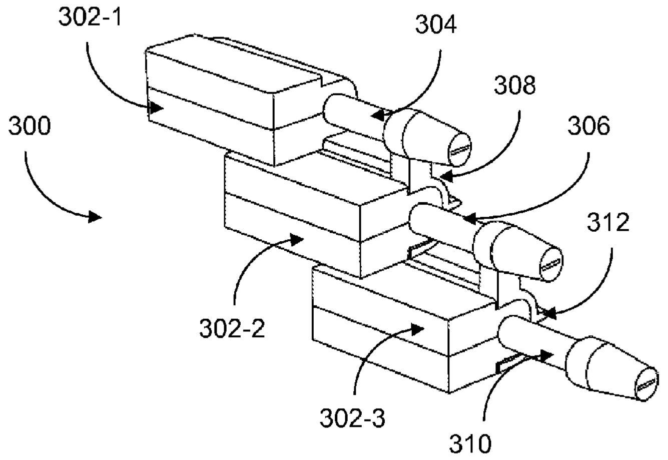
FIG. 3 illustrates motor drives of a motor module arranged in a nested fashion in accordance with an embodiment of the invention.

FIG. 3 illustrates motor drives of a motor module of the one or more motor modules arranged in a nested fashion as described in accordance with an embodiment of the invention. As shown in FIG. 3, a motor module 300 includes multiple motor drives configured in a nested fashion. More specifically, three motor drives such as, a motor drive 302-1, a motor drive 302-2, and a motor drive 302-3 of motor module 300 may be arranged in a nested fashion. It will be apparent to a person skilled in the art that motor module 300 is shown to include three motor drives for purpose of ease of description. However, motor module 300 may include more than three motor drives or less than three motor drives depending on the requirements for manipulating the joints of the limb. Each motor drive of motor module 300 includes a linear actuator and a displacing component operatively coupled to the linear actuator. As shown in FIG. 1, motor drive 302-1 is operatively connected to a linear actuator 304. Further, motor drive 302-2 includes a linear actuator 306 and a displacing component 308 operatively connected to linear actuator 306. Motor drive 302-3 includes a linear actuator 310 and a displacing component 312.

Each motor drive in motor module 300 is displaced by a preceding motor drive in the nested arrangement of the motor drives due to a displacing component of each motor drive. For example, when motor drive 302-1 operates, linear actuator 304 operatively connected to motor drive 302-1 moves in a linear direction. Linear actuator 304 may be connected to displacing component 308 of motor drive 302-2. Thus, when linear actuator 304 moves in the linear direction, displacing component 308 moves to drive motor drive 302-2. Similarly, when motor drive 302-2 is driven, displacing component 312 of motor drive 302-3 is moved by linear actuator 306 of motor drive 302-2 thereby driving motor drive 302-3. By way of another example, if motor drive 302-1 and a linear actuator 304 displace by 20 mm, a motor drive 302-2 and motor drive 302-3 may be displaced by 40 mm and 60 mm respectively, thereby all three motor drives may achieve maximum displacement. Thus, this nested arrangement of motor drives acts as a telescopic linear drive system by displacing each succeeding motor drive when a preceding motor drive is displaced.

Figure 4:
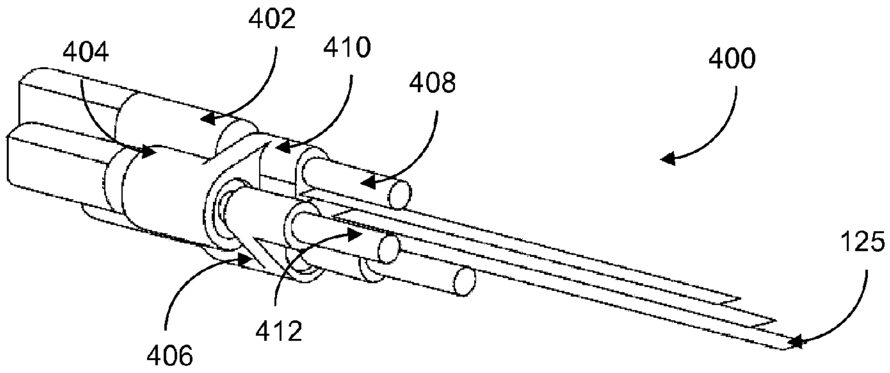
FIG. 4 illustrates motor drives of a motor module arranged in a pyramid fashion in accordance with an embodiment of the invention.

FIG. 4 illustrates motor drives of a motor module 400 of the one or more motor modules arranged in a pyramid fashion as described in accordance with an embodiment of the invention. Motor module 400 includes a plurality of motor drives such as, a motor drive 402, a motor drive 404 and a motor drive 406. Each motor drive of the plurality of motor drives may be cylindrically shaped and arranged in a pyramid fashion. However, it will be apparent to a person skilled in the art that each motor drive may have any other shape.

Motor module 400 further includes a linear actuator connected to each motor drive of the plurality of motor drives. In an embodiment, the linear actuator may include a lead screw and a nut. The lead screw is operatively engaged with a nut. The nut is inturn removably connected to a first end of a fluctuating member. For example, a lead screw 408 may be operatively connected to motor drive 402. Lead screw 408 may be operatively engaged with a nut 410. Nut 410 is removably connected to a first end of actuating member 125. Nut 410 is guided along lead screw 408 in a linear direction in response to driving lead screw 408 by motor drive 402. As nut 410 moves in a linear direction, actuating member 125 also moves in a linear direction. This is explained in detail in conjunction FIG. 3. Nut 410 displaces a nut associated with a succeeding motor drive i.e., motor drive 404 thereby driving a lead screw 412 operatively connected to motor drive 404. The nut connected to the lead screw is further explained in conjunction with FIG. 3.

Figure 5:
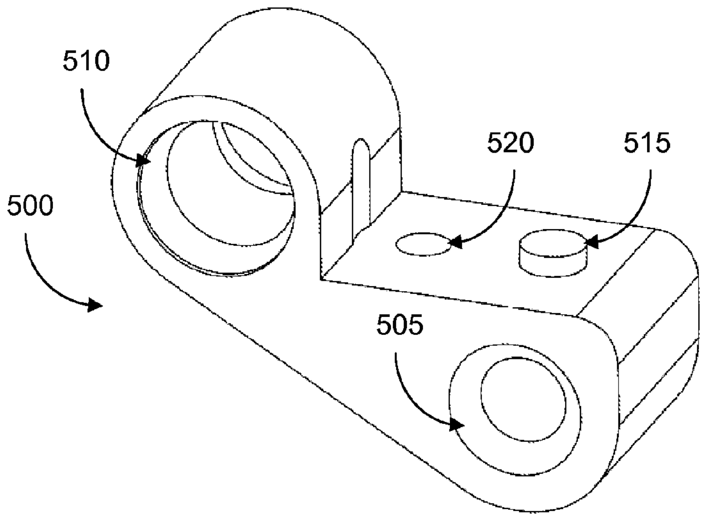
FIG. 5 illustrates a nut that connects different motor drives in the motor module in accordance with an embodiment of the invention.

FIG. 5 illustrates a nut 500 in accordance with an embodiment of the invention. Nut 500 is operatively engaged with a linear actuator of the plurality of linear actuators. Nut 500 may be removably connected to an actuating member. During a linear motion of nut 500 with respect to the linear actuator, nut 500 may guide another similar nut connected to a neighboring linear actuator in apparatus 100. In this case, each succeeding nut of apparatus 100 may be guided by a preceding nut and thus may not require any other external guidance while respective linear actuators move in the linear direction.

Nut 500 includes a threaded hole 505 and a non-threaded hole 510. Threaded hole 505 may be used to operatively engage the linear actuator with nut 500. Whereas, non-threaded hole 510 acts a guide hole that receives the linear actuator operatively connected to a succeeding motor drive. Upon receiving the linear actuator, the linear actuator is slidably engaged with non-threaded hole 510. In an embodiment, non-threaded hole 510 may include one or more entries in form of a ramp in order to provide a smooth guidance of a linear actuator of a succeeding motor drive. During operation, when a linear actuator corresponding to a motor drive drives a nut forward, the nut slides along a linear actuator corresponding to a neighboring motor drive, thereby guiding the neighboring motor drive.

Nut 500 further comprises a protruding member 515 and a screw hole 520. Protruding member 515 and screw hole 520 enable nut 500 to be removably connected to a first end of an actuating member of the plurality of actuating members. The nut has a configuration described above, however the nut may have any other configuration.

Figure 6A:
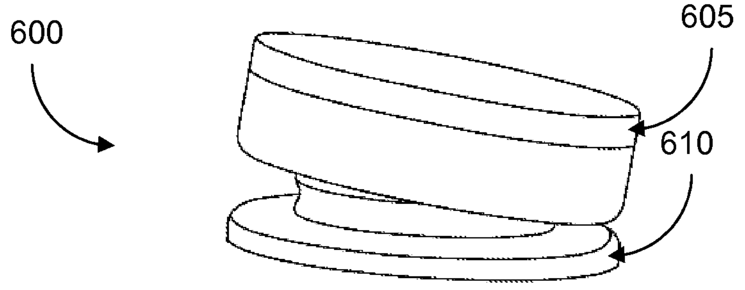
FIG. 6A-FIG. 6B illustrate a magnetic ball segment mount for removably coupling a motor module to a supporting structure.
Figure 6B:
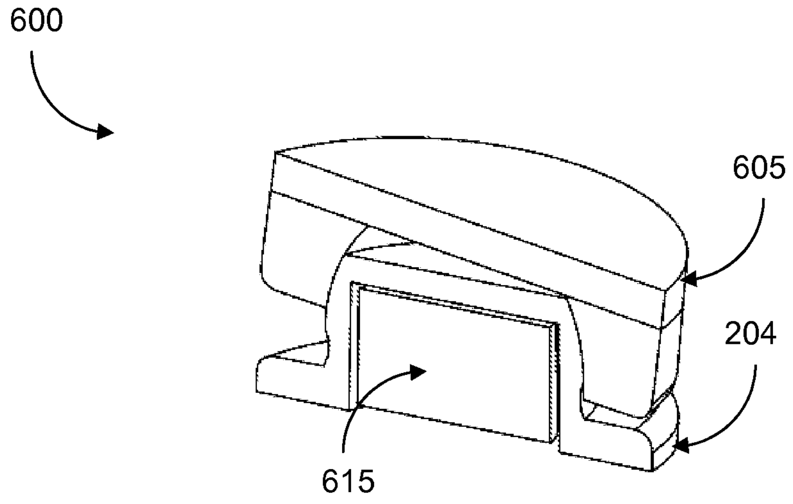

FIG. 6A and FIG. 6B illustrate a magnetic ball segment mount 600 for removably coupling a motor module of the one or more motor modules to the supporting structure. Magnetic ball segment mount 600 includes a first portion 605 and a second portion 610. First portion 605 and second portion 610 may be composed of an Iron based material to attract magnetic force. First portion 605 is attached to a motor module of the plurality of motor modules whereas second portion 610 is removably connected to a guide way such as, guide way 130. A magnet may be attached to a surface of first portion 605. Magnetic ball segment 600 may further include a ball segment with an embedded magnet 615. The ball segment may be attached to second portion 610. The ball segment allows the motor module to have 10 degrees of freedom with respect to a center of the ball segment.

Further, polarity of magnets in first portion 605 and second portion 610 are arranged in a manner that opposite poles face each other. For instance, north pole of a magnet attached to first portion 605 faces a south pole of a magnet attached to second portion 610. Magnetic force between first portion 605 and second portion 610 secures the motor module to splint pad 110. Moreover, the magnetic force between first portion 605 and second portion 610 provides a vertical holding force as well as an angular stability via surface friction. The vertical holding force and the angular stability facilitate in securing the motor module in guide way 130 provided on the surface of splint pad 110.

In an embodiment, magnetic ball segment mount 600 provides a security release option that enables first portion 605 to detach from second portion 610 when the force experienced between first portion 605 and second portion 610 exceeds a predefined force threshold. The predefined force set for detaching first portion 605 and second portion 610 may be adjusted by altering a shape of the ball segment. In an embodiment, the predefined force threshold may be altered or set by a person using the CCU. In this case, the CCU may be equipped with a user interface and buttons for operating the CCU. Further, the predefined force threshold may be set in a time based fashion depending on a physiotherapeutic regime. Thus, the predefined force threshold may be automatically varied by the CCU based on the physiotherapeutic regime. For example, a value associated with a predefined force threshold may be set for a week and then the value may automatically change after one week.

Alternatively, the predefined threshold may automatically change based on the improvement shown in the limb movements of a patient. In this case, the CCU may assess the improvements in the limb movements and changes the predefined force threshold based on the improvements. For example, if the CCU experiences a force that exceeds the predefined force threshold force, it can either stop or reverse the direction of the force exerted by a motor drive.

In an embodiment, a predefined horizontal force threshold and a predefined vertical force threshold may be set. The predefined horizontal force threshold indicates a limit associated with horizontal forces experienced at magnetic ball segment mount 600. Whereas, the predefined vertical force threshold indicates a limit associated with horizontal forces experienced at magnetic ball segment mount 600. In this case, first portion 605 may detach from second portion 610 upon exceeding these set thresholds. Further, the predefined horizontal force threshold and the predefined vertical force threshold may be reset to by altering the shape of the ball segment. For example, the predefined horizontal forces can be adjusted by altering the slope of the surface of the ball segment. Whereas, the predefined vertical threshold forces may be adjusted by altering the grade of magnets used and by a bridging surface area of the ball segment.

In an alternative embodiment, in order to secure the motor modules to splint pad 110, a buckle arrangement is provided. An upper portion of the buckle arrangement may be attached to the motor module and a lower portion of the buckle arrangement may be removably attached onto an upper portion of splint pad 110. The upper portion of the buckle arrangement and the lower portion of the buckle arrangement are attached together in order to secure the motor module to splint pad 110.

Figure 7A:
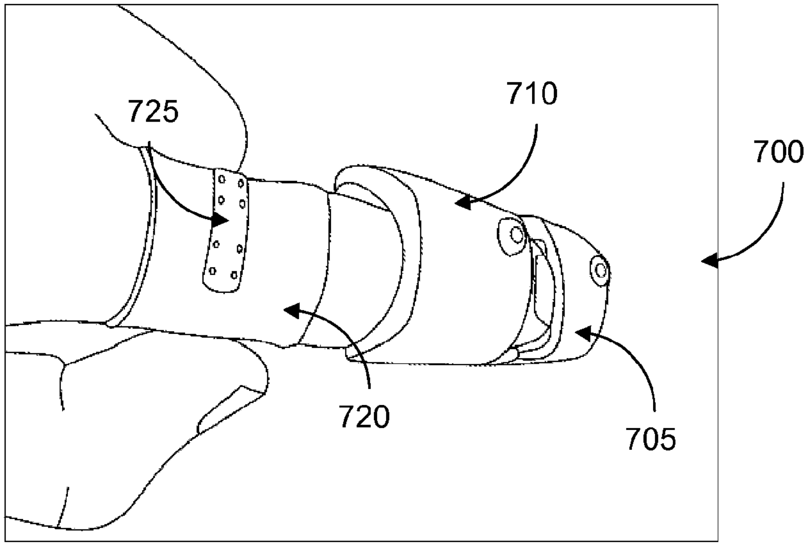
FIG. 7A illustrates a manipulating exoskeleton assembly configured on a digit of a limb in accordance with an embodiment of the invention.
Figure 7B:
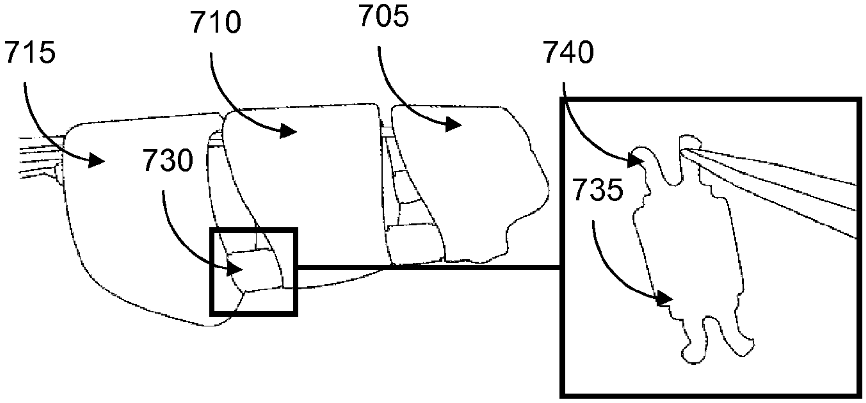
FIG. 7B illustrates a flexure component connecting different exoskeleton segments in the manipulating exoskeleton assembly in accordance with an embodiment of the invention.

FIG. 7A and FIG. 7B illustrate a manipulating exoskeleton assembly 700 configured on a limb such as, a digit as described in accordance with an embodiment of the invention. Manipulating exoskeleton assembly 700 includes a plurality of exoskeleton segments such as, an exoskeleton segment 705, an exoskeleton segment 710, and an exoskeleton segment 715. In an embodiment, an exoskeleton segment of the plurality of exoskeleton segments may be in a form of ringlet. However, the exoskeleton segment may have any other shape and configuration to enable the exoskeleton segment to be conveniently configured on a limb segment of the limb. Exoskeleton segment 705 includes an adhesive component 720 secured to a joint such as, a phalanx segment of the digit. Exoskeleton segment 705 is removably attached to adhesive component 720 thereby disposing exoskeleton segment 705 on the phalanx segment. Adhesive component 720 may be similar to a typical adhesive bandage secured onto a phalanx segment. Adhesive component 720 may have a rib component 725 mounted thereon. Rib component 725 may be removably attached to an upper surface of adhesive component 720. Exoskeleton segment 705 is removably attached to adhesive component 720 by fixing exoskeleton segment 705 onto rib component 725. Such a configuration of an adhesive component is described as one embodiment according to the invention, however, the adhesive component may have any other configuration to conveniently hold an exoskeleton segment to a limb segment of the limb.

Now referring to an exoskeleton segment of the plurality of exoskeleton segments, the exoskeleton segment may be connected to an actuating member. The actuating member may terminate at the exoskeleton segment. As shown in FIG. 7B, an actuating member connected to exoskeleton segment 715 disposed on the phalanx segment such as, a proximal phalanx segment terminates at exoskeleton segment 715. Whereas, an actuating member connected to exoskeleton segment 710 disposed on an intermediate phalanx segment passes through exoskeleton segment 715 and terminates at exoskeleton segment 710. Therefore, exoskeleton segment 715 acts as guide to allow the actuating member connected to exoskeleton segment 710 to pass through. In an embodiment, exoskeleton segment 715 may include a slit to guide the actuating member to terminate at exoskeleton segment 710.

Similarly, an actuating member connected to exoskeleton segment 705 disposed on a distal phalanx segment passes through exoskeleton segment 715 and exoskeleton segment 710 to terminate at exoskeleton segment 705.

In an embodiment, each exoskeleton segment 715 disposed on a phalanx segment is coupled to exoskeleton segment 710 disposed on an adjacent phalanx segment using a flexure component 730. FIG. 7B illustrates a magnified view of flexure component 730 in accordance with the embodiment. Flexure component 730 may provide a flexible link between exoskeleton segment 715 and exoskeleton segment 710. Each opposing side of flexure component 730 forms a virtual rotating axis replicating natural rotating axis of a phalanx segment of the digit. Size and position of flexure component 730 may be optimized in order for flexure component 730 to act in line with the natural rotating axis of a phalanx segment of the digit. Shape of flexure component 730 may be adapted to suit different characteristics, with respect to level of material pliability and shape to control degree of flexibility. Furthermore, flexure component 730 is soft molded to flex with zero elongation. Zero elongation in flexure component 730 is critical for precise delivery of forces to rotate a phalanx segment relative to another phalanx segment. Further, zero elongation in flexure component 730 enables delivering external rotary forces without opposing movements of external segments against the actual joints required to move.

Flexure component 730 includes a flexing member 735 and a plurality of clipping members. A clipping member 740 of the plurality of clipping members is fixedly attached to an end of flexing member 735. The multiple clipping members, attached to flexing member 735, are capable of coupling flexing member 735 to exoskeleton segment 710.

Consider an example where exoskeleton segment 705 is disposed on a distal phalanx segment is coupled to exoskeleton segment 710 disposed on an intermediate phalanx segment using a flexure component 730. Flexure component 730 provides a flexible link that couples exoskeleton segment 705 with exoskeleton segment 710. Therefore, during manipulation of the distal phalanx segment, exoskeleton segment 705 may be able to flex and fold with respect to a distal interphalangeal joint. The flexure component also facilitates achieving angular movement of the distal phalanx segment with respect to the distal interphalangeal joint.

Figure 8A:
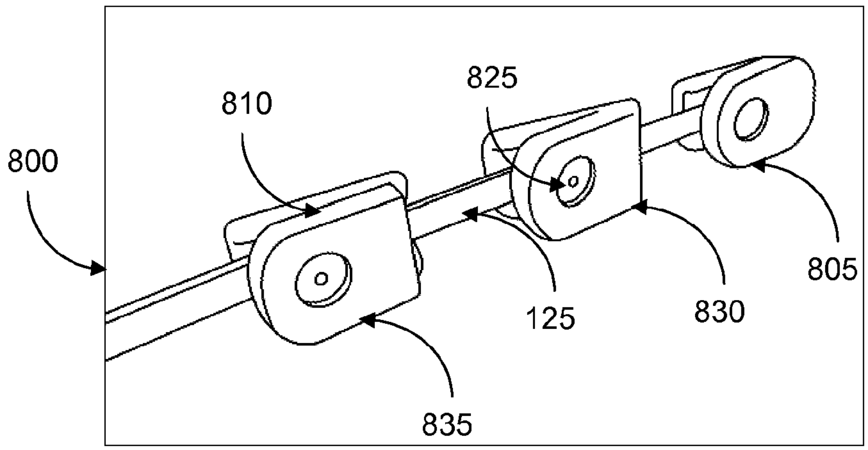
FIG. 8A-FIG. 8B illustrate a manipulating exoskeleton assembly configured on a digit of a limb in accordance with another embodiment of the invention.
Figure 8B:
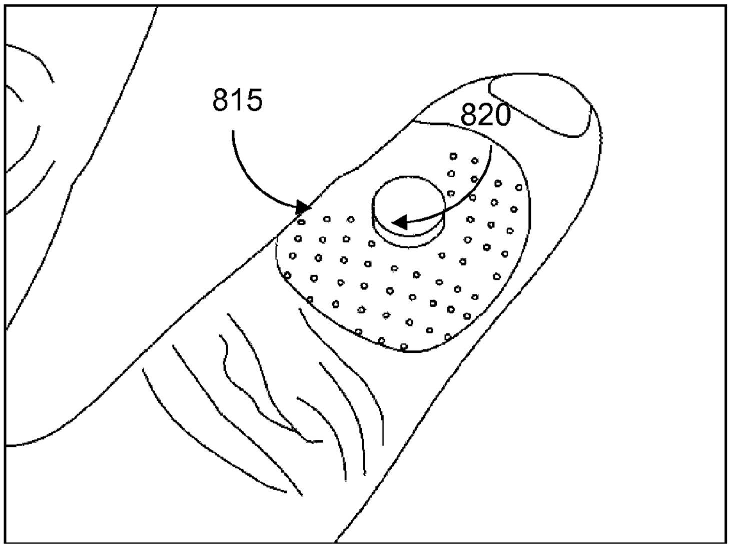

FIG. 8A and FIG. 8B illustrate a manipulating exoskeleton assembly 800 configured on a limb such as, a digit as described in accordance with another embodiment of the invention. In this embodiment, manipulating exoskeleton assembly 800 includes an exoskeleton segment 805 with a molded connector 810. Manipulating exoskeleton assembly 800 also includes an adhesive component 815 removably attached to a phalanx segment, as illustrated in FIG. 8B. Adhesive component 815 may be secured to the phalanx segment in a manner similar to securing a typical adhesive bandage onto a phalanx segment. Adhesive component 815 includes a metal disc 820 embedded onto a surface of adhesive component 815 as shown in FIG. 8B.

Molded connector 810 includes a magnetic component 825 configured therewithin as shown in FIG. 8A. While configuring manipulating exoskeleton assembly 800 on the limb, molded connector 810 may be removably attached to metal disc 820 using magnetic component 825. Thus, exoskeleton segment 805 may be removably attached to adhesive component 815. In an example, magnetic component 825 configured within molded connector 810 may be a rare earth magnet. Molded connector 810 may be then coupled to metal disc 820 due to the magnetic force of magnetic component 825.

During operation of an apparatus such as, apparatus 100 for manipulating joints of the limb, a motor drive associated with the phalanx segment transmits push and pull forces using actuating member 125 such as, actuating member 125-1, actuating member 125-2 and actuating member 125-3, to the phalanx segment of the digit. As the exoskeleton segments such as, exoskeleton segment 805 is coupled to the limb using a magnetic arrangement, this embodiment of the manipulating exoskeleton assembly provides a failsafe mechanism in case forces for manipulating the phalanx segment exceed a threshold limit. When the forces exceed the threshold limit, then exoskeleton segment 805 may disunite from adhesive component 815. More specifically, molded connector 810 may disunite from metal disc 820. Thereafter, exoskeleton segment 805 reunites with adhesive component 815 when actuating member 125 retreats.

Additionally, an exoskeleton segment 830 disposed on an intermediate phalanx segment and an exoskeleton segment 835 disposed on a proximal phalanx segment act as a guide to actuating member 125. For example, exoskeleton segment 830 disposed on an intermediate phalanx segment acts as a guide to actuating member 125 that terminates at a molded connector of exoskeleton segment 805 disposed on distal phalanx segment of the digit.

Figure 9:
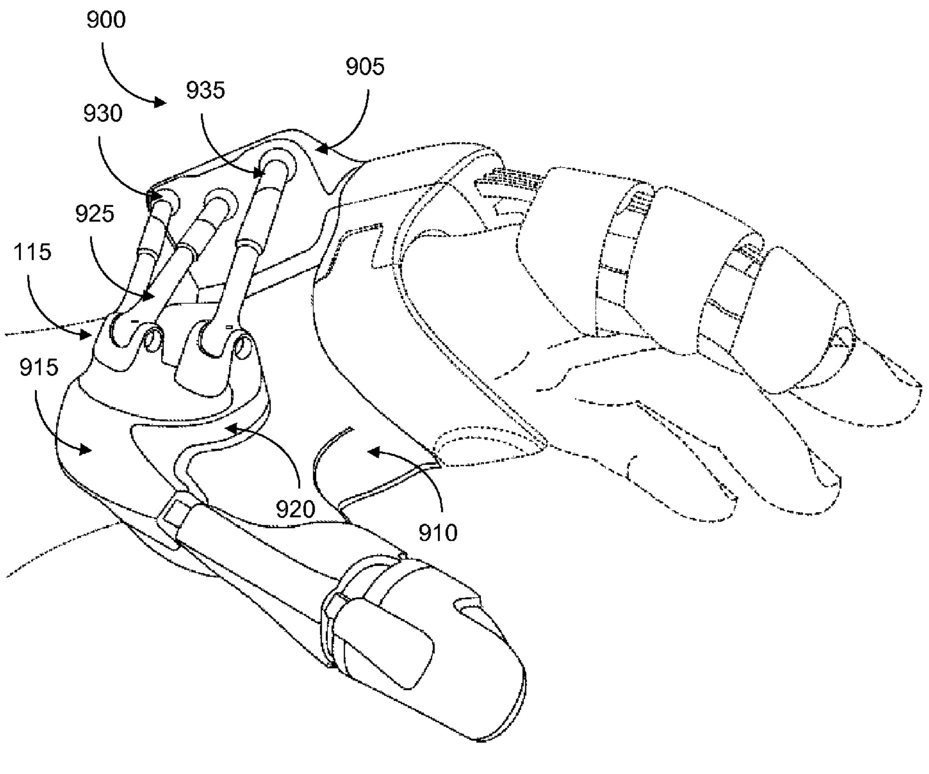
FIG. 9 illustrates a parallel manipulator in accordance with an embodiment of the invention.

Moving to FIG. 9, a parallel manipulator 900 in accordance with an embodiment of the invention is illustrated. Parallel manipulator 900 is used for effectively manipulating phalanx joints of a limb such as, a thumb of the patient. A first end 905 of parallel manipulator 900 is fixedly attached to supporting structure 910 and a second end 915 may be fixedly attached to a grounding component 920 configured on a portion of the limb. For example, grounding component 920 may be removably attached to a metacarpal bone of the thumb. A plurality of motor modules for manipulating the joints of the thumb may be housed in grounding component 920. Parallel manipulator 900 facilitates multiple degrees of freedom of movement for the metacarpal bone of the thumb with respect to supporting structure 910. Parallel manipulator 900 manipulates grounding component 915 and indirectly the metacarpal bone of the thumb to execute movements such as, flexion, extension, abduction, and adduction.

In an embodiment, parallel manipulator 900 is a triple strut drive module. Thus, parallel manipulator 900 may include three linear drives arranged in a cross link manner for facilitating the multiple degrees of freedom of movement for the metacarpal bone of the thumb. These three linear drives include a central drive 925 and two outer drives such as, a drive 930 and a drive 935. Central drive 925 is fixed at first end 905 of parallel manipulator 900 and connected to a universal joint at second end 915 of parallel manipulator 900. The universal joint allows central drive 925 to pitch and yaw about axis of central drive 925. Each of the two outer drives is fixed at first end 905 and connected to a universal ball joint at second end 915. Therefore, each of the two outer drives has 3 degrees of freedom, i.e., pitch, yaw, and roll. Further, each of the two outer drives may be linearly extendable. By controlling ratios of linear extension of each of the three linear drives, a range of angular movements is achieved at second end 915 with respect to first end 905. Thus, the phalanx joints of the thumb can be manipulated in various angles and directions. Further, the cross-link arrangement of the three linear drives enables achieving the desired range of motion necessary for manipulating the phalanx joints of the thumb.

The apparatus disclosed herein, enables manipulation of one or more joints of a limb of a patient. The apparatus includes multiple actuating members, each actuating member being connected to a manipulating exoskeleton assembly removably secured on each joint of the limb. Each actuating member operatively connected to a motor module enables independent manipulation of each joint of the limb. The apparatus provides functional power assistance required for manipulating each joint of the limb to carry out day-to-day activities. Further, in order to control the motor module and subsequently manipulate the joints of the limb, the apparatus includes a central control unit (CCU). The CCU allows independently manipulation each joint of the limb of the patient according to established physiotherapeutic regimes. Furthermore, data associated with the patient may be downloaded by connecting the CCU with a computer system. The data associated with the patient may then be used for monitoring the patient's ability to move the limb.

In the foregoing specification, specific embodiments of the invention have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of the invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. An apparatus for manipulating joints of a limb of a patient, the apparatus comprising:

at least one motor module removably coupled to a supporting structure configured for use on the limb, wherein a motor module of the at least one motor module comprises a plurality of motor drives;

a manipulating exoskeleton assembly comprising a plurality of exoskeleton segments, whereby an exoskeleton segment of the plurality of exoskeleton segments is configured to be removably secured on a limb segment;

a plurality of actuating members operatively connected to each motor module of the at least one motor module, an actuating member of the plurality of actuating members having a first end operatively connected to a motor drive of a motor module of the at least one motor module and a second end removably coupled to an exoskeleton segment of the plurality of exoskeleton segments, whereby upon driving each actuating member of the plurality of actuating members by a motor drive operatively connected to each actuating member push and pull forces are transmitted to a limb segment associated with each actuating member for moving each of the plurality of limb segments thereby independently manipulating the joints of the limb; and a parallel manipulator having a first end attached to the supporting structure and a second end attached to a grounding component configured for attaching to a portion of the limb, the grounding component housing a motor module of the at least one motor module, wherein the parallel manipulator facilitates multiple degrees of freedom of movement with respect to the supporting structure.

2. The apparatus of claim 1, wherein the plurality of motor drives are set up in a stacked arrangement, a child motor drive of the plurality of motor drives is displaced by a parent motor drive in the stacked arrangement of the plurality of motor drives thereby enabling a limb segment associated with the child motor drive to move with respect to a limb segment associated with the parent motor drive.

3. The apparatus of claim 1, further comprising:

a plurality of linear actuators, a linear actuator of the plurality of linear actuators is operatively connected to the motor drive of the plurality of motor drives and connected to an actuating member of the plurality of actuating members, the motor drive capable of driving the linear actuator in a linear direction thereby enabling the actuating member to move in the linear direction.

4. The apparatus of claim 1, wherein a motor module of the at least one motor module is removably coupled to the supporting structure using a stud arrangement thereby enabling the motor module to be adjustably secured to the supporting structure.

5. The apparatus of claim 1, further comprising a magnetic ball component facilitating multiple degrees of freedom of movement for the motor module with respect to the supporting structure.

6. The apparatus of claim 1, wherein an actuating member is a flexible thin gauge strip.

7. The apparatus of claim 1, wherein an exoskeleton segment of the plurality of exoskeleton segments comprises:

at least one adhesive component for attaching to a limb segment; and an exoskeleton component removably attached to an adhesive component of the at least one adhesive component, wherein a second end of an actuating member of the plurality of actuating members is coupled to the exoskeleton component.

8. The apparatus of claim 7, wherein the exoskeleton segment comprises at least one slit, a slit of an exoskeleton segment capable of guiding an actuating member removably coupled to each exoskeleton segment.

9. The apparatus of claim 7, further comprising a plurality of flexure components for coupling an exoskeleton component disposed on a limb segment to an exoskeleton component disposed on an adjacent limb segment, wherein a flexure component of the plurality of flexure components comprises:

a flexing member; and a plurality of clipping members, wherein at least one clipping member of the plurality of clipping members is fixedly attached to each end of the flexing member, the plurality of clipping members capable of coupling the exoskeleton component to the exoskeleton component disposed on the adjacent limb segment.

10. The apparatus of claim 1, wherein an exoskeleton segment of the plurality of exoskeleton segments comprises:

at least one adhesive component for removably attaching to a limb segment of the plurality of limb segments, an adhesive component of the at least one adhesive component having a metal disc embedded thereon; and an exoskeleton component comprising a magnetic component capable of removably attaching to the metal disc for securing the exoskeleton component to the adhesive component, wherein the exoskeleton component is attached to a second end of an actuating member of the plurality of actuating members, the exoskeleton component capable of disuniting from the adhesive component when the force transmitted to the limb segment is beyond a predefined threshold limit.

11. The apparatus of claim 1, further comprising a plurality of force sensors, a force sensor of the plurality of force sensors operatively coupled to a motor housing of a motor drive of the plurality of motor drives, wherein the force sensor measures forces generated at the motor drive during manipulation of a limb segment associated with the motor drive, the forces are measured by determining a torque applied at the limb.

12. The apparatus of claim 11, further comprising a plurality of displacement sensors, a displacement sensor of the plurality of displacement sensors operatively coupled to the motor housing, wherein the displacement sensor measures linear displacement of the motor drive during manipulation of a limb segment associated with the motor drive to determine angular position of the at least one joint of the limb.

13. The apparatus of claim 12, further comprising a central control unit electronically coupled to each motor module of the at least one motor module for controlling the motor module, wherein the central control unit is configured to assess and control manipulation of a limb segment by measuring the forces generated at the motor drive associated with the limb segment and by measuring the displacement of the motor drive during manipulation of a limb segment associated with the motor drive.

14. The apparatus of claim 13, wherein the central control unit is further configured to determine at least one of an absolute displacement of the motor drive, an absolute force of the motor drive, an absolute angle between the joints of the limb, and an absolute torque applied at the limb.

15. An apparatus for manipulating joints of a limb of a patient, the apparatus comprising:

at least one motor module removably coupled to a supporting structure configured for use on the limb, wherein a motor module of the at least one motor module comprises a plurality of motor drives;

a manipulating exoskeleton assembly comprising a plurality of exoskeleton segments, whereby an exoskeleton segment of the plurality of exoskeleton segments is configured to be removably secured on a limb segment;

a plurality of actuating members operatively connected to each motor module of the at least one motor module, an actuating member of the plurality of actuating members having a first end operatively connected to a motor drive of a motor module of the at least one motor module and a second end removably coupled to an exoskeleton segment of the plurality of exoskeleton segments, whereby upon driving each actuating member of the plurality of actuating members by a motor drive operatively connected to each actuating member push and pull forces are transmitted to a limb segment associated with each actuating member for moving each of the plurality of limb segments thereby independently manipulating the joints of the limb; and wherein the plurality of motor drives are set up in a stacked arrangement, a child motor drive of the plurality of motor drives is displaced by a parent motor drive in the stacked arrangement of the plurality of motor drives thereby enabling a limb segment associated with the child motor drive to move with respect to a limb segment associated with the parent motor drive.

* * * * *